(12) United States Patent
Homann et al.

(10) Patent No.: US 9,750,466 B2
(45) Date of Patent: Sep. 5, 2017

(54) DEVICE AND METHOD FOR TOMOSYNTHESIS IMAGING

(71) Applicant: KONINKLIJKE PHILIPS N.V., Eindhoven (NL)

(72) Inventors: Hanno Heyke Homann, Hannover (DE); Frank Bergner, Hamburg (DE); Klaus Erhard, Hamburg (DE); Henning Per Johan Berglund, Sundbyberg (SE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/112,727

(22) PCT Filed: Apr. 16, 2015

(86) PCT No.: PCT/EP2015/058220
§ 371 (c)(1),
(2) Date: Jul. 20, 2016

(87) PCT Pub. No.: WO2015/165737
PCT Pub. Date: Nov. 5, 2015

(65) Prior Publication Data
US 2017/0035372 A1    Feb. 9, 2017

(30) Foreign Application Priority Data

Apr. 29, 2014 (EP) .................................... 14166405

(51) Int. Cl.
*A61B 6/00* (2006.01)
*A61B 6/02* (2006.01)
(Continued)

(52) U.S. Cl.
CPC ............ *A61B 6/025* (2013.01); *A61B 5/0064* (2013.01); *A61B 6/0414* (2013.01);
(Continued)

(58) Field of Classification Search
CPC ........ A61B 5/0064; A61B 6/025; A61B 6/502
See application file for complete search history.

(56) References Cited

U.S. PATENT DOCUMENTS

| 4,896,343 A | 1/1990 | Saunders |
| 9,610,052 B2 | 4/2017 | Nyholm |

(Continued)

FOREIGN PATENT DOCUMENTS

| DE | 102005028415 | 12/2006 |
| FR | 2978911 | 2/2013 |

(Continued)

OTHER PUBLICATIONS

Alvarez, et al., "Energy-Selectrive Reconstructions in X-ray Computerized Tomography", Phys. Med. Biol., 1976, vol. 21, No. 5, 733-744.

*Primary Examiner* — David J Makiya
*Assistant Examiner* — Danielle Fox

(57) ABSTRACT

The present invention relates to a device for tomosynthesis imaging, the device comprising: a mask generator module (101) configured to generate a binary mask based on a geometric three-dimensional model of a scanned object; an image capturing module (102) configured to scan a series of two-dimensional projection images of the object; and an image processing module (103) configured to apply the generated binary mask during a reconstruction of a three-dimensional image volume from the scanned series of two-dimensional projection images and to restrict an extent of the reconstructed image volume to the extent of the geometric model.

13 Claims, 3 Drawing Sheets

(51) Int. Cl.
*A61B 6/04* (2006.01)
*A61B 5/00* (2006.01)
*G06T 11/00* (2006.01)

(52) U.S. Cl.
CPC .......... *A61B 6/4042* (2013.01); *A61B 6/4241* (2013.01); *A61B 6/481* (2013.01); *A61B 6/482* (2013.01); *A61B 6/502* (2013.01); *A61B 6/5205* (2013.01); *A61B 6/5247* (2013.01); *A61B 6/5258* (2013.01); *G06T 11/005* (2013.01)

(56) References Cited

U.S. PATENT DOCUMENTS

| | | | |
|---|---|---|---|
| 2005/0135664 A1* | 6/2005 | Kaufhold | G06T 11/006 382/131 |
| 2007/0183641 A1 | 8/2007 | Peters | |
| 2007/0286470 A1 | 12/2007 | Bernard | |
| 2008/0292217 A1 | 11/2008 | Claus | |
| 2009/0164541 A1 | 6/2009 | Palma | |
| 2014/0031603 A1 | 1/2014 | Robar | |

FOREIGN PATENT DOCUMENTS

| | | |
|---|---|---|
| JP | 2006204329 | 8/2006 |
| JP | 2008/292217 | 12/2008 |
| WO | 2008/074681 | 6/2008 |

\* cited by examiner

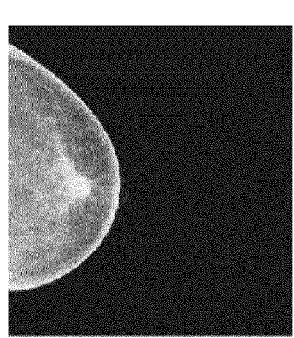 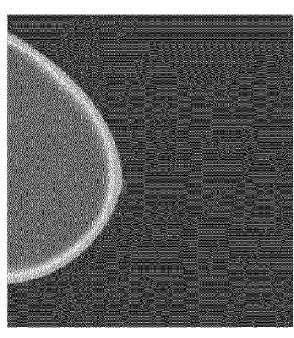 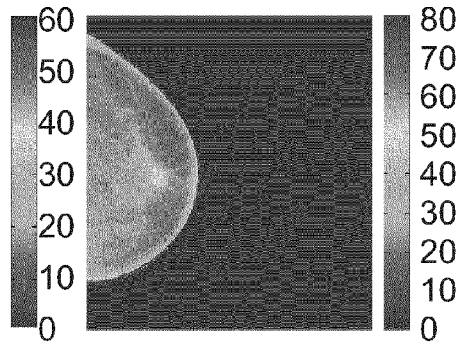
Fig. 4　　　　　Fig. 5　　　　　Fig. 6
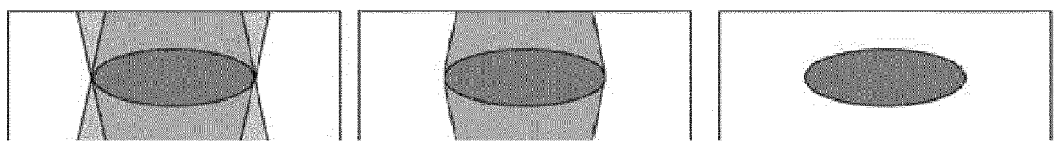
Fig. 7　　　　　Fig. 8　　　　　Fig. 9

DEVICE AND METHOD FOR TOMOSYNTHESIS IMAGING

CROSS REFERENCE TO RELATED APPLICATIONS

This application is the U.S. National Phase application under 35 U.S.C. §371 of International Application No. PCT/EP2015/058220, filed Apr. 16, 2015, published as WO 2015/165737 on Nov. 5, 2015, which claims the benefit of European Patent Application Number 14166405.2 filed Apr. 29, 2014. These applications are hereby incorporated by reference herein.

FIELD OF THE INVENTION

The present invention relates to a device and a method for imaging techniques. In particular, the present invention relates to a device and a method for tomosynthesis imaging.

BACKGROUND OF THE INVENTION

In tomosynthesis, a three-dimensional image volume is reconstructed using X-ray projections from an angular range less than 180°, e.g. typically 10°-60° in human breast tomosynthesis. Due to the limited angular range of the setup, the spatial extent of an object under examination in the principal direction of the X-rays cannot be accurately reconstructed by known image reconstruction techniques.

EP 2,101,648 B1 describes a method and a device for generating a tomosynthetic three-dimensional X-ray image, in which a plurality of digital two-dimensional X-ray projection images are recorded from an examination object with different projection angles in a limited angular range with an X-ray source and a digital X-ray detector, so-called fan artefacts are eliminated by a binary three-dimensional mask, which is determined from the projection image data of a first two-dimensional X-ray image recorded at a first projection angle and the projection image data of a second two-dimensional X-ray image recorded at a second projection angle.

FR 2,978,911 A1 describes a method of illuminating apart of the human body, e.g. a human breast, with low energy radiation in order to acquire a low energy image by an imaging detector. The body part is positioned between the radiation source and the detector. A composite medical image is generated from the low and high energy images by a controller, so that tissues of the body part are displayable in the composite medical image. A system for acquisition and processing of a medical image of a body including an implant is further described.

SUMMARY OF THE INVENTION

There may be a need to improve the digital image processing for tomosynthesis imaging.

These needs are met by the subject-matter of the independent claims. Further exemplary embodiments are evident from the dependent claims and the following description.

An aspect of the invention relates to a device for tomosynthesis imaging, the device comprising: a mask generator module configured to generate a binary mask based on a geometric three-dimensional model of a scanned object; an image capturing module configured to scan a series of two-dimensional projection images of the object; and an image processing module configured to apply the generated binary mask during a reconstruction of a three-dimensional image volume from the scanned series of two-dimensional projection images and to restrict an extent of the reconstructed image volume to the extent of the geometric model.

A further aspect of the invention relates to an X-ray medical imaging system comprising a mammography device and a device for tomosynthesis imaging.

A further aspect of the invention relates to a method for tomosynthesis imaging, the method comprising the steps of: generating a binary mask based on a geometric model of a scanned object; scanning a series of two-dimensional projection images of the object; and applying the generated binary mask to the scanned series of two-dimensional projection images and restricting an extent of each of the reconstructed three-dimensional image volume to the dimensions of the geometric model.

The present invention provides an approach overcome the occurrence of image artifacts outside the object due to the limited angular range. Such artifacts also manifest within the object, e.g. as low frequency intensity variations because the true attenuation cannot be recovered.

The present invention advantageously solves this problem by applying a mask image generated by a binary tomosynthesis reconstruction.

The present invention advantageously also identifies X-rays with a non-zero line-integral value, using the spectral information of these X-rays.

The present invention advantageously provides that the multi-energy projection data can be decomposed into basis material images, e.g. absorptions due to photo-effect and due to Compton-effect. This advantageously allows a quantitative expression of the length of each ray through the object if the volume can be decomposed in mixtures of two materials. This is the case for mammographic volumes, as breast tissue is in most cases a mixture of fatty and glandular tissue. The decomposition can then be expressed as height and glandularity.

If multi-energy projection data are not available, the local height can also be estimated from conventional single-energy projection data for those locations where one tissue type, preferably fatty tissue, dominates. Height information for the other locations can then be obtained by interpolation.

As such height or length information through the volume is available from images taken at different angles; one can reconstruct a binary image volume describing the outer shape of the scanned object. This problem is in general Non-deterministic Polynomial-time hard, in short: NP-hard, but can be relaxed by introducing geometrical priors, e.g. connectedness, smoothness and convexity constraints. Also further boundary conditions are known: The maximum length through the breast is given by the compression height, which is constant over a large area across the breast. And also the skin-line can be correctly delineated at the points where the X-rays are parallel to the skin.

This kind of geometric height model information can be represented as a binary image. This binary image can then be used as a mask in the actual tomosynthesis image formation allows for a better reconstruction of the object extent in the principal X-ray direction and hence improves the tomosynthesis:

allowing a delineation of the breast outline for all slices (i.e. in 3D) and improved background masking; and avoiding the intensity drop towards the breast edge (no need for a post-processing thickness equalization/compensation is given); and reduction of resulting image artifacts inside and outside the imaged object, for instance, the imaged human breast.

In other words, the present invention advantageously proposes to generate a three-dimensional mask image using length information from spectral image decomposition. This removes image artifacts and overcomes the need for thickness equalization.

The method can be used for tomosynthesis images, as it effectively "looks behind the breast" at angles which are outside the coverage of the tomosynthesis scan, which would otherwise be impossible due to the limited tomo-angle, tomo-angle or tomographic angle is the amplitude of tube travel expressed in degrees.

The term "scanned object" or "imaged object" used within the description of the present invention relates to the object to be scanned or any other object or part of the human body, for instance, investigated by Mammography or any other process of using high- or low-energy X-rays to examine the human breast and used as a diagnostic and a screening tool.

The term "energy-resolved X-ray images" or "spectral X-ray images" may be understood as images acquired using any kind of X-ray technique, wherein more than two types of materials can be effectively separated, e.g. with the use of an energy resolved photon-counting detector and classification methodology. Specifically, this applies to the case when contrast agents that contain K-absorption edges in the energy range of interest are present in the object. This separation is enabled via the use of recently developed energy resolved photon-counting detectors with multiple thresholds, which allow simultaneous measurements of the x-ray attenuation at multiple energies.

The binary mask is based on a geometric three-dimensional model of a scanned object mask representing the object's three-dimensional, possibly curved, spatial extent.

According to an exemplary embodiment of the present invention, the mask generator module is configured to generate the binary mask based on the geometric model derived from a laser scanning of the object. This may be combined with intensity information from the projection images.

This advantageously provides an improved matching of the geometric three-dimensional model with the scanned object.

According to an exemplary embodiment of the present invention, the mask generator module is configured to generate the binary mask based on the geometric model derived from image analysis of the at least one two-dimensional projection image of the scanned series of two-dimensional projection images of the object.

This advantageously provides an improved matching of the geometric three-dimensional model with the scanned object.

According to an exemplary embodiment of the present invention, the mask generator module is configured to determine the geometric model of the object based on an intensity profile of the at least one two-dimensional projection image of the object.

This advantageously provides an improved matching of the geometric three-dimensional model with the scanned object.

According to an exemplary embodiment of the present invention, the image capturing module is capable of acquiring energy-resolved X-ray images and the geometric model is derived from a quantitative height model obtained from a spectral material decomposition of the energy-resolved two-dimensional projection images.

According to an exemplary embodiment of the present invention, the mask generator module is configured to generate the binary mask using an object thickness value measured by a mechanical compression unit.

According to an exemplary embodiment of the present invention, the image processing module is configured to apply the generated binary mask during a reconstruction procedure of the scanned series of two-dimensional projection images.

A computer program performing the method of the present invention may be stored on a computer-readable medium. A computer-readable medium may be a floppy disk, a hard disk, a CD, a DVD, an USB (Universal Serial Bus) storage device, a RAM (Random Access Memory), a ROM (Read Only Memory) and an EPROM (Erasable Programmable Read Only Memory). A computer-readable medium may also be a data communication network, for example the Internet, which allows downloading a program code.

The methods, systems and devices described herein may be implemented as software in a Digital Signal Processor, DSP, in a micro-controller or in any other side-processor or as hardware circuit within an application specific integrated circuit, ASIC. The present invention can be implemented in digital electronic circuitry, or in computer hardware, firmware, software, or in combinations thereof, e.g. in available hardware of conventional mobile devices or in new hardware dedicated for processing the methods described herein.

The present invention can be implemented for the use of image reconstruction in various image processing applications and aims at demonstrating the usefulness of this transformation for image altering and segmentation tasks.

A more complete appreciation of the invention and the attendant advantages thereof will be more clearly understood by reference to the following schematic drawings, which are not to scale, wherein.

Figure 1:
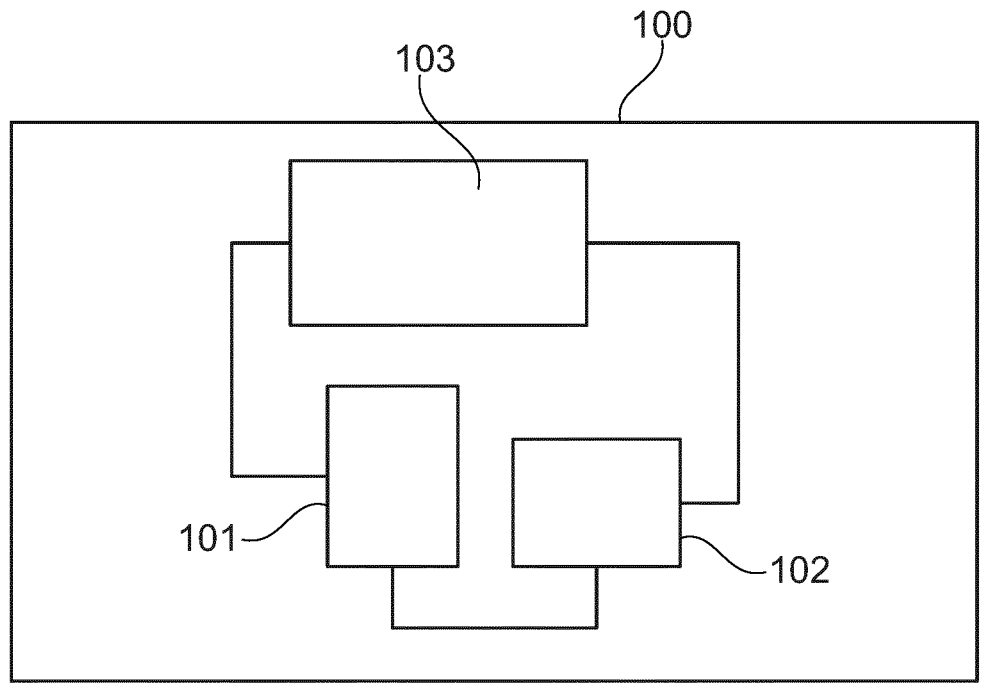
FIG. 1 shows a schematic diagram of a device for tomosynthesis imaging according to an exemplary embodiment of the invention.

FIGS. 4-6 each shows a two-dimensional projection image for explaining the invention; and FIGS. 7-9 each shows a back-projection for explaining the invention.

DETAILED DESCRIPTION OF EMBODIMENTS

The illustration in the drawings is purely schematically and does not intend to provide scaling relations or size information. In different drawings, similar or identical elements are provided with the same reference numerals. Generally, identical parts, units, entities or steps are provided with the same reference symbols in the description.

FIG. 1 shows a schematic diagram of a device for tomosynthesis imaging according to an exemplary embodiment of the invention.

A device 100 for tomosynthesis imaging may comprise a mask generator module 101 configured to generate a binary mask based on a geometric three-dimensional model of a scanned object.

The device 100 may further comprise an image capturing module 102 configured to scan a series of two-dimensional projection images of the object.

Further, the device may comprise an image processing module 103 configured to apply the generated binary mask during a reconstruction of a three-dimensional image volume from the scanned series of two-dimensional projection images and to restrict an extent of the reconstructed image volume to the extent of the geometric model.

Figure 2:
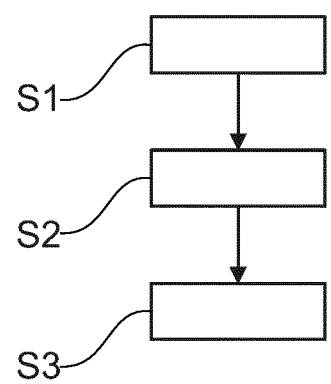
FIG. 2 shows a schematic flowchart diagram of a method for tomosynthesis imaging according to an exemplary embodiment of the invention.

FIG. 2 shows a schematic flowchart diagram of a method for tomosynthesis imaging according to an exemplary embodiment of the invention.

The method is visualized in terms of a block diagram. The method may comprise three steps S1, S2, and S3.

As a first step of the method, generating S1 a binary mask based on a geometric model of a scanned object is conducted.

As a second step of the method, scanning S2 a series of two-dimensional projection images of the object is performed. The step of scanning S2 the series may also be performed prior to the step of generating S1 the binary mask, if, for instance, the geometric model of the scanned object is based on produced projection images which are scanned in the step of scanning S2 the series. If, for instance, the binary mask is generated from an object thickness value measured by a mechanical compression unit, the step of scanning S2 may be performed subsequently to the step of generating S1 the binary mask, as illustrated in the schematic flowchart diagram of FIG. 2.

As a third step of the method, applying S3 the generated binary mask to the scanned series of two-dimensional projection images and restricting an extent of each of the images to the dimensions of the geometric model is performed.

According to an exemplary embodiment of the invention, these steps may be carried out simultaneously, divided into multiple operations or tasks or iterated.

Figure 3:
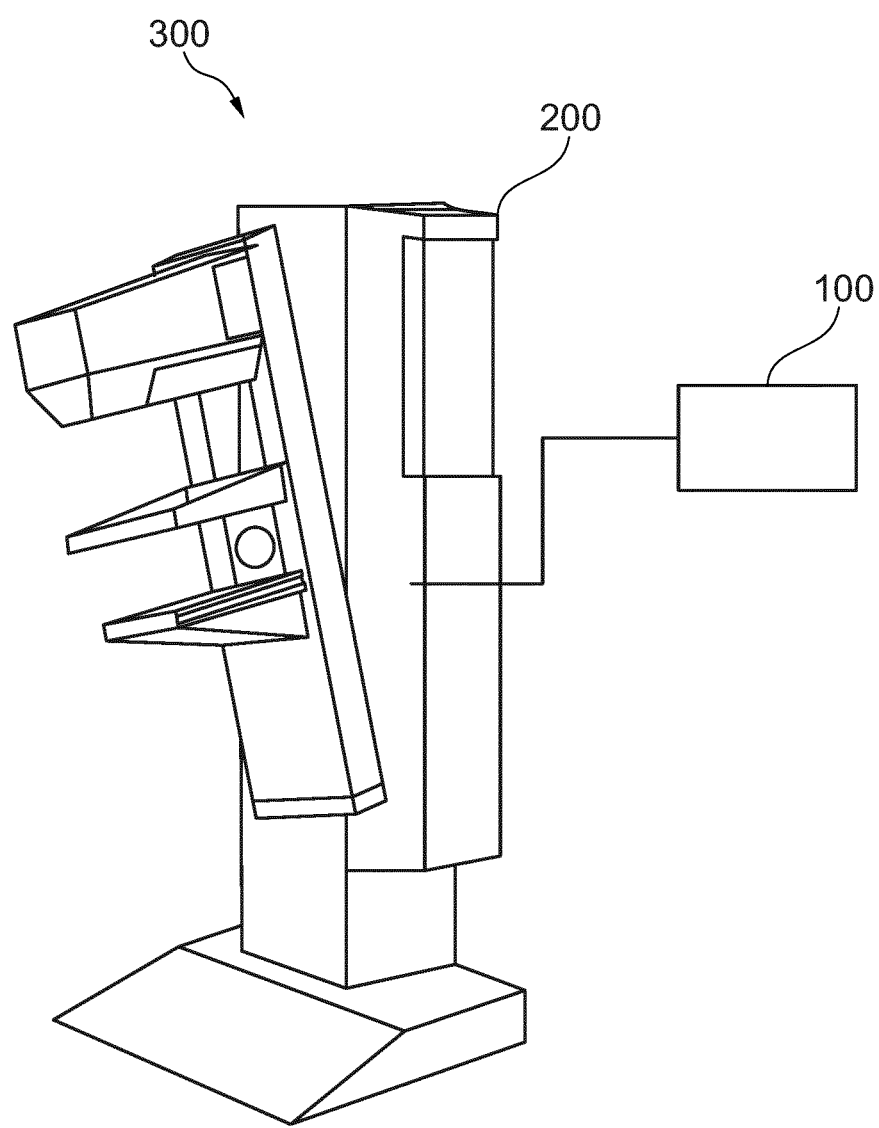
FIG. 3 shows a schematic diagram of an X-ray medical imaging system comprising a mammography device and a device for tomosynthesis imaging according to an exemplary embodiment of the invention.

FIG. 3 shows a schematic diagram of an X-ray medical imaging system comprising a mammography device and a device for tomosynthesis imaging according to an exemplary embodiment of the invention.

An X-ray medical imaging system 300 may comprise a mammography device 200 and a device 100 for tomosynthesis imaging. According to a further exemplary embodiment of the present invention, on the contrary to FIG. 3, the device for tomosynthesis imaging may be integrated to the mammography device 200. Further, also in contrast to the representation of FIG. 3, the medical imaging system 300 may further comprise an operator's computer or a control terminal. The mammography device 200 may comprise a mechanical compression unit, which may contain two plates for compressing the breast during mammography or biopsy.

During the procedure, the breast is compressed using the dedicated mammography device. Parallel-plate compression of the mechanical compression unit evens out the thickness of breast tissue to increase image quality by reducing the thickness of tissue that x-rays must penetrate, decreasing the amount of scattered radiation, scatter degrades image quality, reducing the required radiation dose, and holding the breast still preventing motion blur. Diagnostic mammography may include cranio-caudal, medio-lateral oblique and other views, including geometrically magnified and spot-compressed views of the particular area of concern.

FIGS. 4-6 show a decomposition of spectral mammography data: FIG. 4 shows a two-dimensional projection image for explaining the invention. In FIG. 4, mammogram data is measured with at least two different energy spectra. FIG. 5 shows a decomposition of the spectral mammogram into a height image, the values are given in mm. FIG. 6 illustrates a glandularity image, also obtained by spectral decomposition, showing the percentage of glandular tissue.

According to a further exemplary embodiment of the present invention, the height information is used and taken from different angles to calculate the three-dimensional breast shape.

FIGS. 7-9 show a back-projection for explaining the invention showing cross-section through a tomosynthesis image volume, the principal X-ray direction is from top to bottom.

FIG. 7 shows a tomo-synthesis reconstruction of an elliptical object, e.g. a cross-section through the breast, shaded in dark gray. The spatial extend of the object cannot be reconstructed in the principal X-ray direction, leading to artifacts, the X-rays represented by the light gray areas, but also by artifacts within the object. FIG. 8 shows a reconstruction using a binary mask obtained pure by identification of background rays which can reduce the artifacts. FIG. 9 shows a reconstruction using binary mask generated from a geometric model, e.g. by the spectral height image in FIG. 5 in combination with binary spectral tomosynthesis, recovering the true object outline, thus also reducing artifacts within the object.

The term "binary spectral tomosynthesis" refers to a reconstruction of a binary three-dimensional volume representing the object's spatial extent using spectral mammography projection images.

In another exemplary embodiment of the present invention, a computer program or a computer program element is provided that is characterized by being adapted to execute the method steps of the method according to one of the preceding embodiments, on an appropriate system.

According to a further exemplary embodiment of the present invention, the computer program element might therefore be stored on a computer unit, which might also be part of an embodiment of the present invention. This computing unit may be adapted to perform or induce a performing of the steps of the method described above.

Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention. This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it, which computer program element is described by the preceding section.

The present invention may be used for X-ray tomosynthesis in different medical fields, like, for instance, breast imaging, chest imaging, or dental imaging. A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network.

According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims.

However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art and practicing the claimed invention, from a study of the drawings, the disclosure, and the appended claims.

In the claims, the word "comprising" does not exclude other elements or steps, and the indefinite article "a" or "an" does not exclude a plurality. A single processor or controller or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

The invention claimed is:

1. A device for tomosynthesis imaging, the device comprising:
    a mask generator module configured to generate a binary mask based on a geometric three-dimensional model of a scanned object, derived from a laser scanning of the object;
    an image capturing module configured to scan a series of two-dimensional projection images of the object; and
    an image processing module configured to apply the generated binary mask during a reconstruction of a three-dimensional image volume from the scanned series of two-dimensional projection images and to restrict an extent of the reconstructed image volume to the extent of the geometric model.

2. The device for tomosynthesis imaging according to claim 1, wherein the mask generator module is configured to generate the binary mask based on the geometric model derived from image analysis of at least one two-dimensional projection image of the scanned series of two-dimensional projection images of the object.

3. The device for tomosynthesis imaging according to claim 2, wherein the mask generator module is configured to determine the geometric model of the object based on an intensity profile of the at least one two-dimensional projection image of the object.

4. The device for tomosynthesis imaging according to claim 1, where the image capturing module is capable of acquiring energy-resolved two-dimensional X-ray protection images and the geometric model is derived from a quantitative height model obtained from a spectral material decomposition using the energy-resolved two-dimensional X-ray projection images.

5. The device for tomosynthesis imaging according to claim 1, wherein the mask generator module is configured to generate the binary mask using an object thickness value measured by a mechanical compression unit.

6. The device for tomosynthesis imaging according to claim 1, wherein the image processing module is configured to apply the generated binary mask during a reconstruction procedure of the scanned series of two-dimensional projection images.

7. An X-ray medical imaging system comprising a mammography device and a device for tomosynthesis imaging according to claim 1.

8. A method for tomosynthesis imaging, the method comprising the steps of:
    generating a binary mask based on a geometric model of a scanned object, derived from a laser scanning of the object;
    scanning a series of two-dimensional projection images of the object; and
    applying the generated binary mask to the scanned series of two-dimensional projection images and restricting an extent of each of the images to the dimensions of the geometric model.

9. The method for tomosynthesis imaging according to claim 8, wherein the step of generating the binary mask based on the geometric model further comprises deriving from image analysis of the at least one two-dimensional projection image of the scanned series of two-dimensional projection images of the object.

10. The method for tomosynthesis imaging according to claim 8, wherein the step of generating the binary mask based on the geometric model further comprises determining the geometric model of the object based on a intensity profile of the at least one two-dimensional projection image of the object.

11. The method for tomosynthesis imaging according to claim 8, where the step of generating the binary mask based on the geometric model further acquiring energy-resolved two-dimensional X-ray projection images, wherein the geometric model is derived from a quantitative height model obtained from a spectral material decomposition of the energy-resolved two-dimensional X-ray projection images.

12. The method for tomosynthesis imaging according to claim 8, wherein the step of generating the binary mask based on the geometric model further comprises deriving a geometric model using an object thickness value measured by a mechanical compression unit.

13. The method for tomosynthesis imaging according to claim 8, wherein the method further comprises the step of generating a binary mask during a reconstruction procedure using the scanned series of two-dimensional projection images.

* * * * *